United States Patent [19]

Snyder, Jr. et al.

[11] 4,043,926

[45] Aug. 23, 1977

[54] LUBRICANT COMPOSITION

[75] Inventors: Carl E. Snyder, Jr., Trotwood; Christ Tamborski, Dayton, both of Ohio

[73] Assignee: The United States of America as represented by the Secretary of the Air Force, Washington, D.C.

[21] Appl. No.: 681,871

[22] Filed: Apr. 30, 1976

Related U.S. Application Data

[63] Continuation-in-part of Ser. No. 629,469, Nov. 6, 1975.

[51] Int. Cl.$^2$ .............................................. C10M 3/24
[52] U.S. Cl. ................................. 252/49.9; 252/49.6; 252/49.8; 260/606.5 P
[58] Field of Search .................... 252/49.9, 49.8, 49.6; 260/606.5 P

[56] References Cited

U.S. PATENT DOCUMENTS

| | | | |
|---|---|---|---|
| 3,393,151 | 7/1968 | Dolle et al. | 252/49.9 |
| 3,481,872 | 12/1969 | Dolle et al. | 252/49.9 |
| 3,483,129 | 12/1969 | Dolle et al. | 252/49.9 |
| 3,499,041 | 3/1970 | Tamborski | 260/606.5 P |
| 3,567,802 | 3/1971 | Garth | 252/49.9 |

*Primary Examiner*—Arthur P. Demers
*Attorney, Agent, or Firm*—Joseph E. Rusz; Cedric H. Kuhn

[57] ABSTRACT

A lubricant comprising a perfluorinated polyalkylether base fluid and a minor amount of a perfluoroalkylether substituted aryl phosphine.

11 Claims, No Drawings

LUBRICANT COMPOSITION

RIGHTS OF THE GOVERNMENT

The invention described herein may be manufactured and used by or for the Government of the United States for all governmental purposes without the payment of any royalty.

This application is a continuation-in-part of application Ser. No. 629,469, filed on Nov. 6, 1975.

FIELD OF THE INVENTION

This invention relates to lubricant compositions based upon perfluorinated polyalkylether base fluids and containing a perfluoroalkylether substituted aryl phosphine anti-corrosion additive.

BACKGROUND OF THE INVENTION

Because of their thermal stability, perfluorinated polyalkylether fluids have a great potential for use as engine oils, hydraulic fluids and greases. However, a serious drawback in their use results from the fact that certain metals, e.g., certain ones present in aircraft engine components, are corroded at temperatures above 550° F in an oxidative environment. For example, when the fluids are employed as lubricants for mechanical components composed of mild steels, serious corrosion has occured at temperatures of from 550° to 600° F. Furthermore, stainless steels, titanium and titanium alloys are attacked by the fluids at a temperature of about 600° F. Moreover, when used with titanium and titanium alloys, the fluids themselves undergo negative viscosity changes to the detriment of continued lubricating capacity.

In U.S. Pat. No. 3,393,151, issued to one of us as a coinventor on July 16, 1968, lubricants are disclosed that comprise a perfluorinated aliphatic polyether and a perfluorophenyl phosphorus compound. In U.S. Pat. No. 3,499,041, issued to one of us on Mar. 3, 1970, certain perfluoroarylphosphines are disclosed as being anti-corrosion additives for perfluorinated fluids. While the phosphorus compounds described in these patents exhibit anti-corrosion properties, at low temperatures they are only poorly soluble in perfluorinated fluids. Also, certain members of the classes of phosphorus compounds possess high volatility characteristics for long term high temperature applications. Because of these limitations, perfluorinated fluids containing such anti-corrosion additives are not completely satisfactory for use in long term, wide temperature range ($-100°$ F to $>600°$ F) applications.

Accordingly, it is an object of this invention to provide an improved lubricant composition containing, as a base fluid, a perfluorinated polyalkylether.

Another object of the invention is to provide a lubricant composition that has little or no corrosive effect upon ferrous and titaniium alloys.

A further object of the invention is to provide a lubricant composition which undergoes substantially no degradation when exposed to titanium.

Still another object of the invention is to provide a lubricant composition which can be used at temperatures ranging from about $-100°$ F to 700° F.

Other objects and advantages of the invention will be apparent to those skilled in the art upon consideration of the accompanying disclosure.

SUMMARY OF THE INVENTION

The present invention resides in a lubricant composition comprising a perfluorinated polyalkylether base fluid and a corrosion inhibiting amount of a perfluoroalkylether substituted aryl phosphine. The phosphorus compound additive exhibits excellent solubility in the base fluid and possesses outstanding low volatility characteristics. As a result, the lubricant composition functions as a noncorrosive, stable material suitable for long term applications over a wide temperature range ($-100°$ F to $>600°$ F) in an oxidative environment.

In general, any suitable perfluorinated polyalkylether can be used as a base fluid in formulating the lubricant of this invention. However, it is preferred to utilize a compound having the following formula:

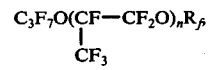

where $R_f$ is a perfluoroalkyl group containing 2 or 3 carbon atoms and $n$ is an integer ranging from 5 to 50, inclusive, preferably from about 10 to 40, inclusive. The value of $n$ is usually such that the compound has a molecular weight ranging from about 2000 to 7000 and a kinematic viscosity ranging from about 15 to 500 centistokes at 100° F. Perfluorinated polyalkylethers corresponding to the aforementioned formula are commercially available compounds that are described in the literature. For a detailed description of a method for preparing the compounds, reference may be made to U.S. Pat. No. 3,242,218.

The perfluoroalkylether substituted aryl phosphines (fluorinated phosphines) used as corrosion inhibitors in the lubricant composition of this invention have the following formula:

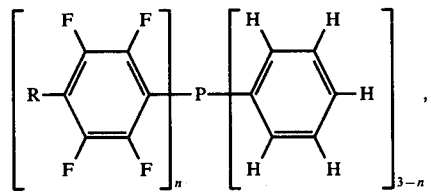

where R is a perfluoroalkylether group ($CF_2R_fOR_f$) or fluorine, with two of the R's being fluorine, and $n$ is 1, 2 or 3.

The preferred fluorinated phosphines are those in which the perfluoroalkylether group is para to the phosphorus atom. In general, R can be any perfluoroalkylether group as long as the group contains at least one ether linkage. However, it is often preferred that the group contain two or more ether linkages. Examples of perfluoroalkylether groups include the following where $R_fOR_f$ may be:

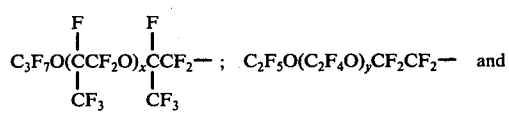

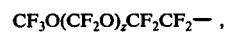

where x, y and z are zero or an integer from 1 to 20, inclusive, preferably an integer from 1 to 4, inclusive.

The procedure followed in preparing completely fluorinated phosphines, i.e., when $n$ in the above formula equals 3, can be represented by the following equations:

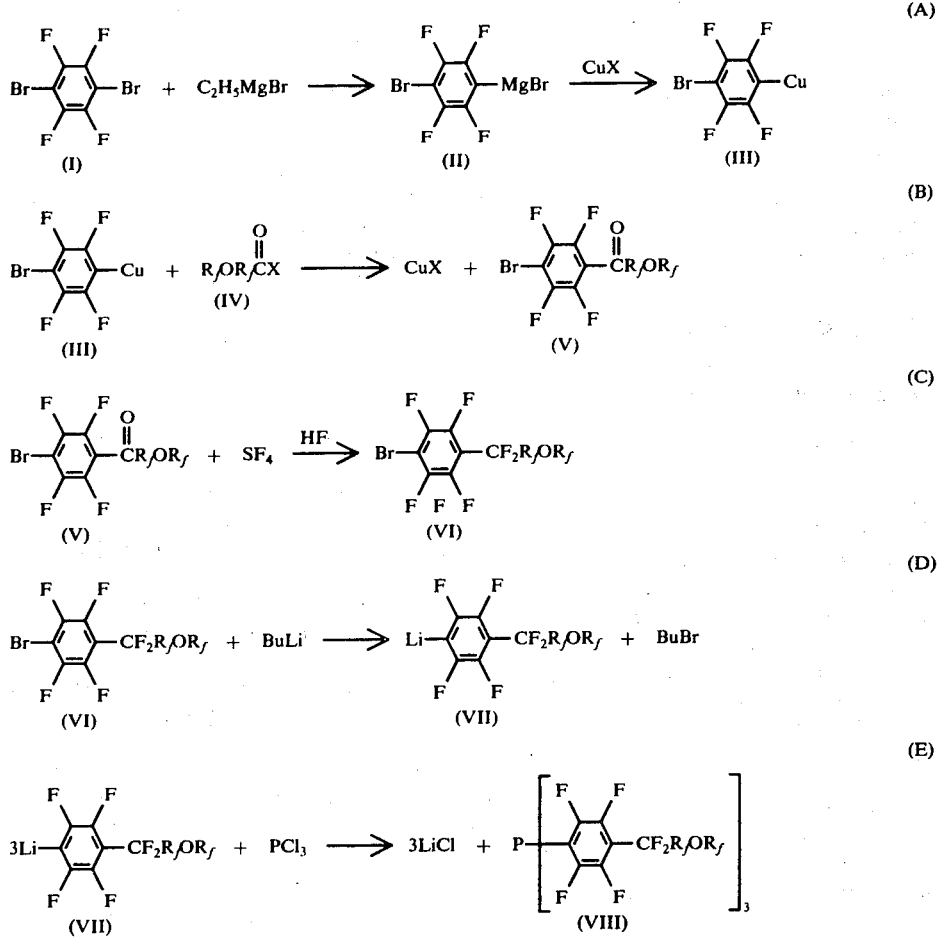

As seen from equation (A), 1,4-dibromotetrafluorobenzene is reacted with ethylmagnesium bromide. The reaction is carried out by mixing solutions of the compounds in suitable solvents under conditions such as to form compound (II), e.g., at about $-5°$ to $5°$ C for about 15 minutes to 1 hour. Thereafter, a cuprous halide is added to the reaction mixture whose temperature is then allowed to rise to room temperature. The cuprous halide reacts with compound (II), thereby forming organocopper compound (III).

The organocopper compound is an intermediate which can react with perfluoroacyl halides to yield a variety of ketones. The reaction that occurs is shown by equation (B). In carrying out the indicated reaction, the perfluoroacyl fluoride (IV) is added to the organocopper compound (III) which has been cooled to about $-5°$ to $5°$ C. The compounds are usually allowed to react at room temperature for a period of about 12 to 14 hours after which the reaction mixture is hydrolyzed. After extracting the mixture with a solvent for the ketone product (V), the solvent layer is phase separated and dried. The ketone is then recovered by fractional distillation.

As shown by equation (C), the ketone is fluorinated by reacting same with sulfur tetrafluoride. This reaction is accomplished by adding anhydrous hydrogen fluoride and sulfur tetrafluoride to a cooled pressure vessel containing the ketone. The sealed pressure vessel is then rocked and maintained at a temperature ranging from about 150 to 200° C for a period of about 12 to 24 hours. After cooling and venting the vessel, its contents are washed with a solvent. The solvent is then evaporated, and the residue is fractionally distilled to yield fluorinated product (VI).

In accordance with equation (D), n-butyllithium is added to a solution of perfluoroalkylether compound (VI) at $-70°$ to $-80°$ C. In the reaction that ensues, which generally takes from 15 minutes to 1 hour, the bromine atom of compound (VI) is replaced with a lithium atom, thereby forming perfluorinated compound (VII). At the end of the reaction period, a solution of phosphorus trichloride is added to compound (VII), and the reaction that occurs yields a phosphine compound (VIII) of this invention. In the reaction as depicted by equation (E), the reaction mixture is stirred at about $-70°$ to $-80°$ C for about 0.5 to 1.5 hours after which it is allowed to warm slowly to about $-25°$ to $-35°$ C over a period of about 3 to 10 hours. Recovery of the product is accomplished by adding dilute hydrochloric acid to the reaction mixture which is phase separated. The bottom viscous layer is washed with water, diluted with a fluorinated solvent and then dried. After filtration and removal of solvent, phosphine product (VIII) is obtained by fractional distillation in the form of a viscous liquid.

The materials used in preparing the intermediates and the phosphine products are known compounds that are described in the literature. The foregoing equations illustrate the preparation of para substituted compounds. However, it is also within the scope of the invention to use the meta and ortho isomers as anti-corrosion additives in the lubricant composition. In synthesizing the meta and ortho isomers, 1,3- and 1,2-dibromotetrafluorobenzene, respectively, are utilized as a starting material rather than 1,4-dibromotetrafluorobenzene.

Any acyl halide can be used that corresponds to the formula $R_fOR_fC(O)X$, where $R_fOR_f$ is a perfluoroalkylether group and X is a halogen. Examples of suitable acyl halides, which are a source of the $R_fOR_f$ groups, are disclosed in U.S. Pat. Nos. 3,124,599, 3,214,478 and 3,721,696. Thus, depending upon the acyl halide employed, a variety of ketones can be synthesized according to the reaction illustrated by equation (B). As shown by equation (C), the ketone is fluorinated with sulfur tetrafluoride so that its ketone group becomes a $CF_2$ group. Thus, in the above formula defining the fluorinated phosphines used as corrosion inhibitors in the lubricant compositions of this invention, R equals $CF_2R_fOR_f$ where this group appears in the foregoing equations.

The foregoing description has been concerned with completely fluorinated phosphines. However, it is within the purview of the present invention to use as the anti-corrosion additives partially fluorinated phosphines, i.e., when n in the above formula is 1 or 2. The same procedure as described above is followed in preparing the partially fluorinated phosphines except that in the reaction illustrated by equation (E) phenyldichlorophosphine (n=2) or diphenylchlorophosphine (n=1) is reacted with compound (VII) instead of phosphorus trichloride. The reaction involved can be represented by the following equation:

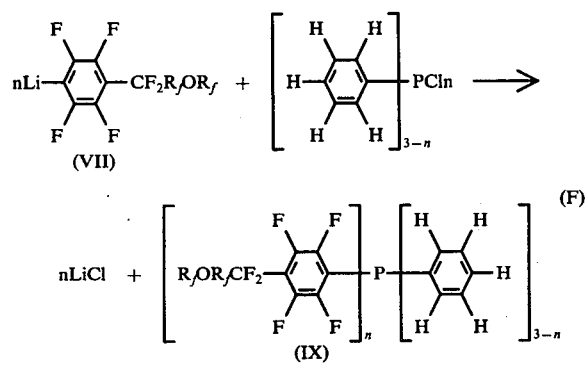

In equation (F), n equals 1 or 2.

A more detailed description of the synthesis of the fluorinated phosphines is contained in our copending U.S. patent application Ser. No. 629,469, filed on Nov. 6, 1975. The disclosure of that application is incorporated herein by reference.

In formulating the lubricant of this invention, a corrosion inhibiting amount of the phosphine compound is mixed with the perfluorinated polyalkylether base fluid. The amount of the phosphine compound used generally ranges from about 0.05 to 5 weight percent, preferably 0.5 to 2 weight percent, based upon the weight of the base fluid. The lubricant composition is characterized by the fact that the phosphine anti-corrosion additives are soluble at low temperatures, e.g., at $-65°$ F, in the base fluid and are substantially non-volatile at elevated temperatures. As a result, there is provided a lubricant containing an amount of anti-corrosion additive that is adequate for long term applications at elevated temperatures while still maintaining excellent formulation stability after storage at low temperatures for long periods of time.

A more comprehensive understanding of the invention can be obtained by referring to the following illustrative examples which are not intended, however, to be unduly limitative of the invention.

EXAMPLE I

A series of tests was conducted for the purpose of demonstrating the effectiveness of a fluorinated phosphine of this invention as an anti-corrosion additive for a perfluorinated polyalkylether base fluid. Lubricant compositions were formulated by mixing (1) a base fluid having the following formula:

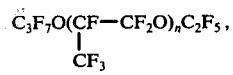

where n is an integer having a value such that the fluid has a kinematic viscosity of 258.4 at 100° F with (2) various weight percentages, based upon the weight of the base fluid, of a fluorinated phosphine having the following formula:

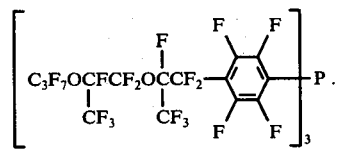

The base fluid used was Krytox 143AC fluid, a product of E. I. duPont de Nemours and Company, Wilmington, Del.

In the tests a specimen of steel, titanium, or titanium alloy was immersed in the formulations that were prepared. The compositions of the steel and titanium alloys used as specimens are described in the literature. For comparison purposes, tests were also carried out in which specimens were immersed in the polyether fluid which did not contain the anti-corrosion additive. The materials were contained in an oxidation test tube having a take-off adapter coupled to an air entry tube. An aluminum block bath provided the means for heating the test tube and an "overboard" test procedure (no reflux condenser) was followed.

Air was bubbled through the formulations, or in the case of the control tests through the polyether fluid, at the rate of one liter of air per hour for a period of 24 hours. The tests were conducted at a constant temperature of 600° F, 625° F or 650° F. The specimens as well as the apparatus used were weighed prior to and after completion of each test.

The data obtained in the tests are set forth below in the tables.

TABLE I

600° F.

| Wt. % Additive | Kinematic Viscosity Change at 100° F, % | Fluid Loss Wt. % | Weight Change, mg/cm² | | | | |
|---|---|---|---|---|---|---|---|
| | | | 4140 Steel | 52100 Bearing Steel | 410 Stainless Steel | M-50 Tool Steel | 440C Stainless Steel |
| none | 17.4 | 5.4 | +2.64 | +1.13 | −1.08 | −2.08 | −2.57 |
| 0.5 | 1.9 | 0.04 | +0.15 | +0.01 | +0.02 | +0.02 | −0.01 |
| 1.0 | 3.0 | 0.14 | +0.13 | +0.06 | +0.01 | +0.10 | 0.00 |
| 2.0 | 1.9 | 0.07 | +0.01 | +0.02 | +0.01 | −0.01 | 0.00 |
| 625° F |||||||||
| none | 3.7 | 21.0 | −5.41 | −7.50 | −7.72 | −5.51 | −10.75 |
| 1.0 | 4.8 | 0.22 | +0.13 | 0.00 | −0.02 | +0.07 | 0.00 |
| 650° F |||||||||
| none | 1.0 | 10.6 | −7.11 | +0.26 | +4.13 | −4.78 | −7.20 |
| 1.0 | 2.3 | 0.5 | +0.05 | +0.12 | +0.01 | +0.31 | +0.06 |

TABLE II

| Temp, °F | Wt. % Additive | Kinematic Viscosity Change at 100° F, % | Fluid Loss Wt. % | Weight Change, mg/cm² | | |
|---|---|---|---|---|---|---|
| | | | | Ti(6A14V) | Ti(pure) | Ti(4A14Mn) |
| 600 | None | 37 | 19.5 | +0.21 | −0.16 | −0.68 |
| 600 | 1.0 | 2.8 | 0.5 | +0.04 | +0.03 | +0.05 |
| 625 | None | 90 | 48.1 | +0.20 | −0.57 | −1.72 |
| 625 | 1.0 | 4.8 | 0.4 | +0.04 | +0.04 | +0.05 |

EXAMPLE II

Runs were conducted in which lubricant compositions were tested by the same procedure described in Example I. The lubricant compositions tested were formulated by mixing the same polyether base fluid used in Example I with various weight percentages of several fluorinated phosphine additives. The following fluorinated phosphines were used in formulating the lubricants:

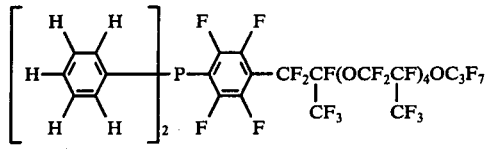

(A)

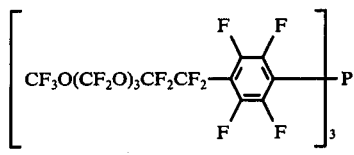

(B)

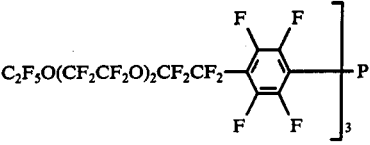

(C)

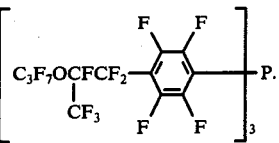

(D)

The concentrations of the additives (A), (B), (C) and (D), the test temperatures and the results obtained in the tests are shown below in Table III.

TABLE III

| Additive & Concentration, Wt % | Temp °F | Kinematic Viscosity Change at 100° F (%) | Acid Number Change (mgKOH/g) | Fluid Loss % | Metal Weight Change (mg/cm²) | | | | |
|---|---|---|---|---|---|---|---|---|---|
| | | | | | 4140 Steel | 521000 Bearing Steel | 410 Stainless Steel | M-50 Tool Steel | 440C Stainless Steel |
| (A) |||||||||| 
| 0.5% | 625 | +2.47 | <0.1 | 0.09 | +0.05 | +0.02 | +0.04 | +0.06 | +0.01 |
| 1.0% | 625 | +3.24 | <0.1 | 0.29 | +0.07 | +0.05 | +0.02 | +0.12 | +0.14 |
| 2.0% | 625 | +0.49 | <0.1 | 0.09 | +0.11 | +0.15 | +0.04 | +0.10 | +0.01 |
| 2.0% | 650 | +1.22 | <0.1 | 0.37 | +0.12 | +0.28 | +0.14 | +0.13 | +0.04 |
| (B) |||||||||| 
| 1.0% | 625 | +4.19 | <0.1 | 0.16 | 0.00 | +0.03 | 0.00 | +0.01 | +0.08 |
| (C) |||||||||| 
| 1.0% | 625 | +3.58 | <0.1 | 0.25 | +0.03 | +0.01 | +0.02 | +0.01 | +0.02 |
| (D) |||||||||| 
| 1.0% | 625 | +2.14 | <0.1 | 0.35 | +0.05 | +0.05 | 0.00 | +0.07 | +0.02 |
| 1.0% | 650 | +1.68 | <0.1 | 0.51 | +0.19 | +0.19 | +0.06 | −0.28 | +0.08 |

The data in the foregoing tables demonstrate that the lubricant compositions of this invention have little if any corrosive effect upon titanium and ferrous and titanium alloys. Furthermore, there was substantially no degradation of the base fluid itself at the elevated temperatures of the tests. Because of these outstanding properties and the solubility of the phosphine additives, the lubricants can be employed in applications requiring extreme temperature conditions. Examples of uses for the lubricants include (1) gas turbine engine lubricants (−20° to 650° F), (2) nonflammable hydraulic fluids (−20° to 700° F), greases compatible with liquid oxygen (30° to 600° F), and liquid coolants and general purpose lubricants (−100° to 700° F).

As will be evident to those skilled in the art, modifications of the present invention can be made in view of the foregoing disclosure without departing from the spirit and scope of the invention.

We claim:

1. A lubricant composition comprising (1) a perfluorinated polyalkylether base fluid and (2) a corrosion inhibiting amount of a phosphine compound having the following formula:

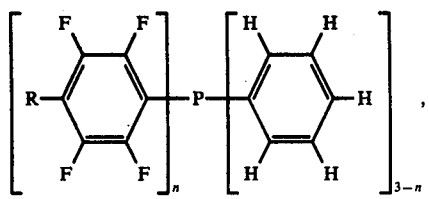

where one of the R's is a perfluoroalkylether group, two of the R's are fluorine, and *n* is 1, 2 or 3.

2. The lubricant composition according to claim 1 in which the amount of the phosphine compound ranges from about 0.05 to 5 weight percent, based upon the weight of the base fluid.

3. The lubricant composition according to claim 1 in which the amount of the phosphine compound ranges from about 0.5 to 2.0 weight percent, based upon the weight of the base fluid.

4. The lubricant composition according to claim 1 in which the perfluorinated polyalkylether base fluid is a compound having the following formula:

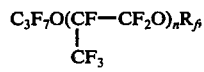

where $R_f$ is a perfluoroalkyl group containing 2 or 3 carbon atoms and *n* is an integer ranging from 5 to 50, inclusive.

5. The lubricant composition according to claim 4 in which the R group of the phosphine compound is

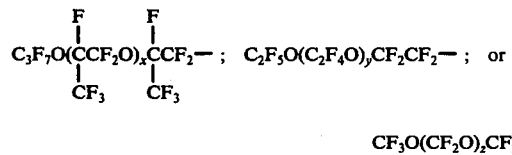

$$CF_3O(CF_2O)_zCF_2CF_2\text{—},$$

where *x*, *y* and *z* are zero or an integer from 1 to 20, inclusive.

6. The lubricant composition according to claim 5 in which the phosphine compound has the following formula:

7. The lubricant composition according to claim 5 in which the phosphine compound has the following formula:

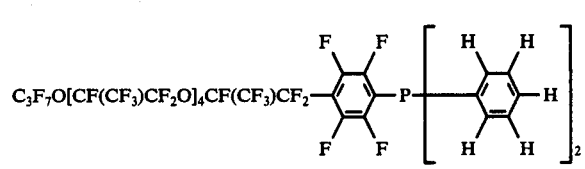

8. The lubricant composition according to claim 5 in which the phosphine compound has the following formula:

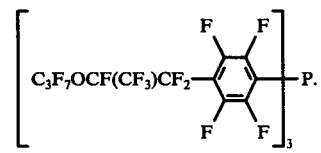

9. The lubricant composition according to claim 5 in which the phosphine compound has the following formula:

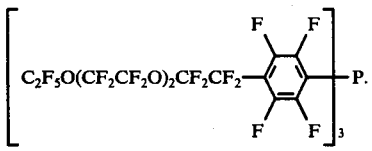

10. The lubricant composition according to claim 5 in which the phosphine compound has the following formula:

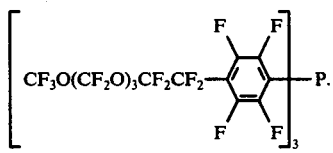

11. The lubricant composition according to claim 5 in which the phosphine compound has the following formula:

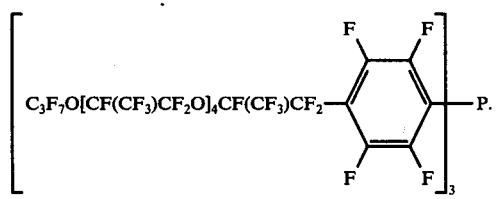

* * * * *

UNITED STATES PATENT AND TRADEMARK OFFICE
CERTIFICATE OF CORRECTION

PATENT NO. : 4,043,926

DATED : August 23, 1977

INVENTOR(S) : Carl E. Snyder, Jr. and Christ Tamborski

It is certified that error appears in the above-identified patent and that said Letters Patent are hereby corrected as shown below:

Column 1, line 59, "titaniium", should read -- titanium --. Column 2, lines 40 to 47, the formula should read as follows:

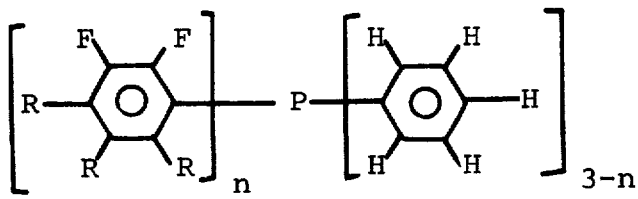

Column 7 and 8, Table III, "521000", should read -- 52100 --.
Column 9, lines 1 to 10, the formula should read as follows:

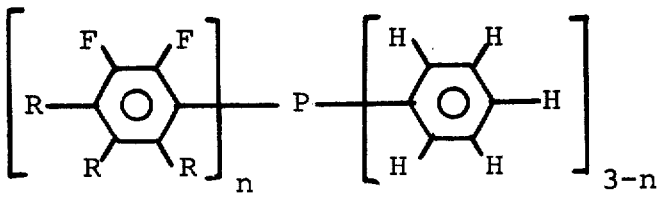

Signed and Sealed this

Seventh Day of February 1978

[SEAL]

Attest:

RUTH C. MASON
Attesting Officer

LUTRELLE F. PARKER
Acting Commissioner of Patents and Trademarks